(12) United States Patent
Terui et al.

(10) Patent No.: US 11,531,122 B2
(45) Date of Patent: Dec. 20, 2022

(54) RADIATION IMAGING APPARATUS AND IMAGING SYSTEM

(71) Applicant: CANON KABUSHIKI KAISHA, Tokyo (JP)

(72) Inventors: Kosuke Terui, Yokohama (JP); Atsushi Iwashita, Tokyo (JP); Akira Tsukuda, Kawasaki (JP); Sota Torii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/080,959

(22) Filed: Oct. 27, 2020

(65) Prior Publication Data

US 2021/0041584 A1 Feb. 11, 2021

Related U.S. Application Data

(63) Continuation of application No. PCT/JP2019/010047, filed on Mar. 12, 2019.

(30) Foreign Application Priority Data

May 29, 2018 (JP) .............................. JP2018-102615

(51) Int. Cl.
*G01T 1/20* (2006.01)
*H04N 5/32* (2006.01)
*A61B 6/00* (2006.01)

(52) U.S. Cl.
CPC ........... *G01T 1/20184* (2020.05); *H04N 5/32* (2013.01); *A61B 6/4266* (2013.01)

(58) Field of Classification Search
CPC ...... G01T 1/20184; H04N 5/32; A61B 6/4266
See application file for complete search history.

(56) References Cited

U.S. PATENT DOCUMENTS

| | | | | |
|---|---|---|---|---|
| 4,425,031 A | * | 1/1984 | Tamura | .................... G02B 7/32 250/201.5 |
| 6,710,803 B1 | * | 3/2004 | Kang | .................. H04N 5/3575 348/245 |

(Continued)

FOREIGN PATENT DOCUMENTS

| JP | H04-086165 A | 3/1992 |
|---|---|---|
| JP | 2002-344809 A | 11/2002 |

(Continued)

OTHER PUBLICATIONS

U.S. Appl. No. 16/103,150, Atsushi Iwashita, dated Aug. 14, 2018.

(Continued)

*Primary Examiner* — Blake C Riddick
(74) *Attorney, Agent, or Firm* — Venable LLP (57) ABSTRACT

A radiation imaging apparatus, comprising a sensor array in which a plurality of sensor units are arranged and a driving unit for driving the sensor array, wherein each sensor unit includes u detection element for detecting radiation and a sampling unit configured to be able to sample a signal from the detection element, the sampling unit is connected to a signal line configured to propagate a signal from the detection element, the driving unit uses the sampling unit to perform a first sampling driving operation and a second sampling driving operation to sample the signal propagating through the signal line, and the driving unit starts the second sampling driving operation before the completion of the first sampling driving operation and completes the second sampling driving operation after the completion of the first sampling driving operation.

21 Claims, 6 Drawing Sheets

(56) References Cited

U.S. PATENT DOCUMENTS

| | | | |
|---|---|---|---|
| 7,667,745 B2 | 2/2010 | Watanabe | |
| 7,692,704 B2* | 4/2010 | Hashimoto | H04N 5/378 348/302 |
| 9,048,154 B2 | 6/2015 | Takenaka et al. | |
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,541,653 B2 | 1/2017 | Iwashita et al. | |
| 9,655,586 B2 | 5/2017 | Yagi et al. | |
| 9,737,271 B2 | 8/2017 | Iwashita et al. | |
| 9,812,474 B2 | 11/2017 | Yagi et al. | |
| 9,820,711 B2 | 11/2017 | Tsukuda et al. | |
| 9,971,046 B2 | 5/2018 | Ryu et al. | |
| 9,980,685 B2 | 5/2018 | Iwashita et al. | |
| 9,989,656 B2 | 6/2018 | Sato et al. | |
| 10,009,990 B2 | 6/2018 | Takenaka et al. | |
| 10,070,082 B2 | 9/2018 | Tsukuda et al. | |
| 10,197,684 B2 | 2/2019 | Terui et al. | |
| 10,274,612 B2 | 4/2019 | Ishii et al. | |
| 10,441,238 B2 | 10/2019 | Terui et al. | |
| 10,779,777 B2 | 9/2020 | Terui et al. | |
| 10,782,251 B2 | 9/2020 | Sato et al. | |
| 2004/0013232 A1* | 1/2004 | Rahn | H04N 3/155 348/E3.018 |
| 2004/0169753 A1 | 9/2004 | Gulbransen et al. | |
| 2004/0213377 A1* | 10/2004 | Endo | A61B 6/482 257/E27.132 |
| 2006/0214699 A1* | 9/2006 | Watanabe | H04N 5/30 327/72 |
| 2007/0153109 A1 | 7/2007 | Lule | |
| 2008/0083876 A1* | 4/2008 | Endo | H04N 5/378 250/369 |
| 2008/0232549 A1* | 9/2008 | Poorter | A61B 6/5264 378/98.9 |
| 2009/0009635 A1* | 1/2009 | Maeda | H04N 5/378 348/241 |
| 2009/0140157 A1* | 6/2009 | Meng | G01T 1/2018 250/370.11 |
| 2009/0323897 A1* | 12/2009 | Kameshima | H04N 5/325 378/116 |
| 2010/0079648 A1* | 4/2010 | Totsuka | H04N 5/3742 348/308 |
| 2010/0194948 A1* | 8/2010 | Murakami | H04N 5/3658 348/302 |
| 2010/0252717 A1 | 10/2010 | Dupont et al. | |
| 2012/0006993 A1* | 1/2012 | Arishima | H04N 5/3575 250/369 |
| 2012/0075507 A1* | 3/2012 | Yamazaki | H04N 5/32 348/241 |
| 2012/0087471 A1* | 4/2012 | Naito | H04N 5/37452 378/62 |
| 2012/0104267 A1* | 5/2012 | Matsumoto | H04N 5/33 250/370.08 |
| 2013/0001429 A1* | 1/2013 | Dowaki | H04N 5/3765 250/394 |
| 2013/0083227 A1* | 4/2013 | Murata | H04N 5/3745 348/308 |
| 2013/0193334 A1* | 8/2013 | Dowaki | H04N 5/32 250/370.09 |
| 2013/0327950 A1* | 12/2013 | Niwa | H04N 5/3745 250/395 |
| 2014/0029721 A1* | 1/2014 | Niwa | G01T 1/24 378/62 |
| 2014/0036118 A1* | 2/2014 | Dowaki | H04N 5/2173 348/294 |
| 2014/0117204 A1* | 5/2014 | Ha | H04N 5/37452 250/208.1 |
| 2014/0239186 A1 | 8/2014 | Sato et al. | |
| 2014/0361189 A1 | 12/2014 | Kameshima et al. | |
| 2015/0001394 A1* | 1/2015 | Yamazaki | H04N 5/32 250/336.1 |
| 2015/0204988 A1* | 7/2015 | Dowaki | H04N 5/3456 378/62 |
| 2015/0288890 A1 | 10/2015 | Senda et al. | |
| 2015/0296151 A1* | 10/2015 | Dowaki | H04N 5/343 250/370.08 |
| 2015/0316661 A1* | 11/2015 | Fujiyoshi | G01T 1/2018 378/62 |
| 2015/0373292 A1* | 12/2015 | Ikawa | H04N 5/3559 250/208.1 |
| 2015/0378034 A1* | 12/2015 | Dowaki | H04N 5/32 250/394 |
| 2016/0104733 A1* | 4/2016 | Sato | H04N 5/3559 250/208.1 |
| 2016/0131772 A1* | 5/2016 | Sato | G01N 23/04 378/62 |
| 2016/0134822 A1* | 5/2016 | Kosonen | H04N 5/374 348/308 |
| 2016/0139276 A1* | 5/2016 | Naito | G01T 1/2018 250/393 |
| 2016/0270755 A1 | 9/2016 | Takenaka et al. | |
| 2017/0019617 A1* | 1/2017 | Dowaki | H04N 5/3653 |
| 2018/0128755 A1 | 5/2018 | Iwashita et al. | |
| 2019/0179036 A1 | 6/2019 | Takenaka et al. | |
| 2019/0320993 A1 | 10/2019 | Noda et al. | |
| 2019/0349541 A1 | 11/2019 | Iwashita et al. | |
| 2020/0124749 A1 | 4/2020 | Takenaka et al. | |
| 2020/0150059 A1 | 5/2020 | Torii et al. | |
| 2020/0150286 A1 | 5/2020 | Terui et al. | |
| 2020/0155097 A1 | 5/2020 | Torii et al. | |
| 2020/0211238 A1 | 7/2020 | Iwashita et al. | |
| 2020/0245441 A1 | 7/2020 | Tsukuda et al. | |

FOREIGN PATENT DOCUMENTS

| | | |
|---|---|---|
| JP | 2006-253789 A | 9/2006 |
| JP | 2009-504221 A | 2/2009 |
| JP | 2016-163244 A | 9/2016 |
| WO | 2007/017773 A2 | 2/2007 |
| WO | 2013/065680 A1 | 5/2013 |
| WO | 2014/054546 A1 | 4/2014 |

OTHER PUBLICATIONS

U.S. Appl. No. 16/986,841, Asato Kosuge, dated Aug. 6, 2020.
U.S. Appl. No. 17/091,008, Takeshi Noda, dated Nov. 6, 2020.
U.S. Appl. No. 17/127,302, Sota Torii, dated Dec. 18, 2020.

* cited by examiner

RADIATION IMAGING APPARATUS AND IMAGING SYSTEM

CROSS-REFERENCE TO RELATED APPLICATIONS

This application is a Continuation of International Patent Application No. PCT/JP2019/010047, filed Mar. 12, 2019, which claims the benefit of Japanese Patent Application No. 2018-102615, filed May 29, 2018. both of which are hereby incorporated by reference herein in their entirety.

BACKGROUND OF THE INVENTION

Field of the Invention

The present invention relates to a radiation imaging apparatus and an imaging system.

Background Art

Among radiation imaging apparatuses, there is a radiation imaging apparatus in which each sensor unit of a sensor array includes, together with a radiation detection element, two or mere sampling units for sampling a signal from the radiation detection element. Such a radiation imaging apparatus is used to perform radiation imaging which is referred to as, for example, an energy subtraction method (see PTL 1). According to the energy subtraction method, two sets of image data are obtained for the same object (for example, a patient), and a single radiation image is formed based on the weighted subtraction result of these image data. For example, two sets of image data are obtained under different radiation intensities from each other, a desired target part (for example, an organ) is observed by performing arithmetic processing using a predetermined coefficient, and the observation target can be changed (for example, from an organ to a bone) by changing the coefficient.

CITATION LIST

Patent Literature

PTL 1 Japanese Patent Laid-Open No. 2009-504221

In the arrangement of the above-described sensor unit including the sampling units, the sampling units are required to have equal sampling characteristics to improve the signal sampling accuracy.

An object of the present invention is to provide a technique advantageous in improving a sampling accuracy in an arrangement in which each sensor unit of a sensor array includes sampling units.

SUMMARY OF THE INVENTION

An aspect of the present invention relates to a radiation imaging apparatus, comprising: a sensor array in which a plurality of sensor units are arranged; and a driving unit configured to drive the sensor array, w herein each of the plurality of sensor units includes a detection element configured to detect radiation and a sampling unit configured to be able to sample a signal from the detection element, the sampling unit is connected to a signal line configured to propagate a signal front the detection element, the driving unit uses the sampling unit to perform a first sampling driving operation and a second sampling driving operation to sample the signal propagating through the signal line, and the driving unit starts the second sampling driving operation before the completion of the first sampling driving operation and completes the second sampling driving operation after the completion of the first sampling driving operation.

Further features of the present invention will become apparent from the following description of exemplary embodiments with reference to the attached drawings.

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

First Embodiment

Figure 1A:
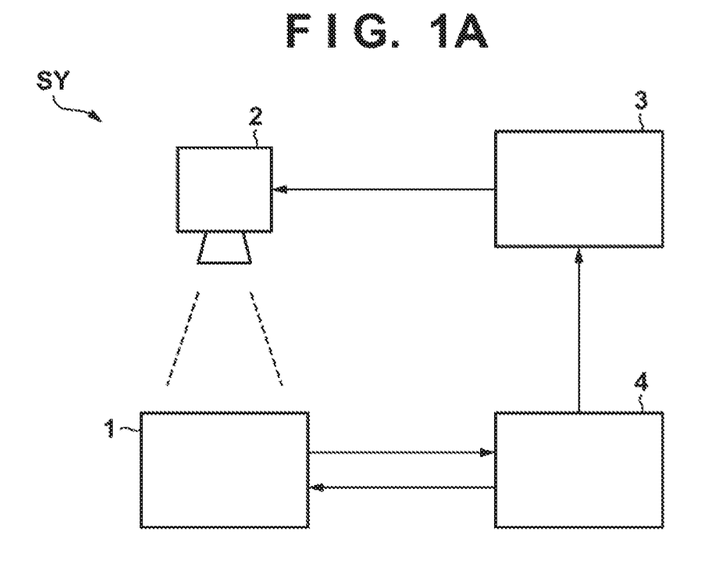
FIG. 1A is a block diagram stowing an example of the arrangement of a radiation imaging system and a radiation imaging apparatus.

FIG. 1A shows an example of a radiation imaging system SY according to the first embodiment. In this embodiment, the radiation imaging system SY includes a radiation imaging apparatus 1, a radiation source 2, a radiation control unit 3, and an arithmetic processing apparatus 4. The radiation imaging apparatus 1 is configured to be able to execute radiation imaging. The radiation source 2 generates radiation. Although an X-ray is typically used as the radiation, another electromagnetic wave such as an α-ray, a β-ray, or the like may lie used. The radiation control unit 3 performs driving control of the radiation source 2. The arithmetic processing apparatus 4 is configured to be able to communicate with the radiation imaging apparatus 1 and drive the radiation source 2 by the radiation control unit 3, and performs the control of the overall radiation imaging system SY.

For example, the arithmetic processing apparatus 4 is connected to an operation unit (not shown), and a user such as a doctor or a radiographer can input imaging information required to perform radiation imaging. This imaging information includes, for example, information indicating a part (an internal organ) to be the inspection target, control information (for example, information indicating the control parameters) of the radiation imaging apparatus 1 and the radiation source 2 for implementing radiation imaging on this part. The arithmetic processing apparatus 4 sets the initial settings of the radiation imaging apparatus 1 based on this imaging information, drives the radiation source 2 via the radiation control unit 3 after the imaging start preparation has been completed in the radiation imaging apparatus 2, and perform imaging by the radiation imaging apparatus 2. The radiation imaging apparatus 1 generates image data indicating the intracorporeal information of a subject (not shown) based on the radiation that has been emitted from the radiation source 2 and has passed through the patient. Furthermore, the arithmetic processing apparatus 4 is connected to a display unit (not shown) and causes this display unit to display a radiation image based on the image data received from the radiation imaging apparatus 1.

The radiation source 2 is configured to change the radiation intensity with time (to be described in detail later), and the arithmetic processing apparatus 4 is configured to be able to notify the radiation imaging apparatus 1 of the change of the radiation intensity and tbc timing thereof in this embodiment. The radiation imaging apparatus 1 can receive information indicating such mode of change of the radiation intensity from the arithmetic processing apparatus 4 and control the operation of each element of the radiation imaging apparatus 1 based on this information.

Although a general-purpose computer including a CPU (Central Processing Unit), a memory, and an external communication interface is used as the arithmetic processing apparatus 4, a semiconductor apparatus such as an ASIC (Application Specific Integrated Circuit), a PLD (Programmable Logic Device), or the like may be used. That is, the functions of the arithmetic processing apparatus 4 can be implemented by either hardware or software.

Figure 1B:
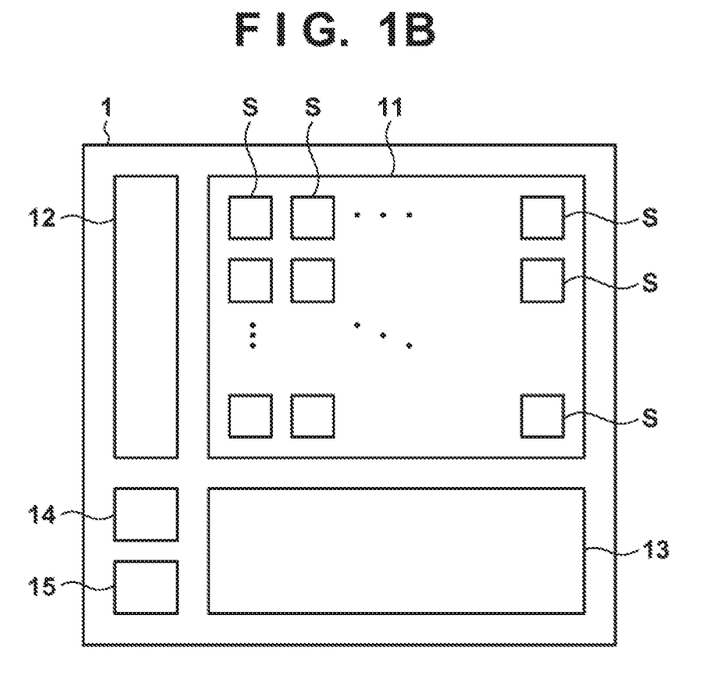
FIG. 1B is a block diagram stowing an example of the arrangement of the radiation imaging system and the radiation imaging apparatus.

FIG. 1B shows an example of the arrangement of the radiation imaging apparatus 1. In this embodiment, the radiation imaging apparatus 1 includes a sensor array 11, a driving unit 12, a readout unit 13, a control unit 14, and a power supply unit 15. The sensor array 11 includes a plurality of sensor units S arranged so as to form a plurality of rows and a plurality of columns. Although the details will be described later, each sensor unit S is configured to be able to detect radiation and generates a signal (sensor signal) corresponding to the accumulated irradiation amount (radiation dose) of radiation.

Although it is not shown here, a scintillator is arranged on a surface on the side of the radiation source 2 of the sensor array 11, and the scintillator generates light (scintillation light) of an amount corresponding to the radiation dose. Each sensor unit S generates a sensor signal by detecting the scintillation light. That is, in this embodiment, a method of converting radiation into light and convening the light into an electrical signal which is a so-called indirect conversion method is applied to the sensor array 11.

The driving unit 12 is configured to be able to drive the sensor array 11, and can drive the plurality of sensor units S for each row in this embodiment. The readout unit 13 is configured to be able to execute a signal readout operation from the sensor array 11, and can read out the sensor signals of the plurality of sensor units S for each column that have been driven by the driving unit 12 in this embodiment. For example, a vertical scanning circuit can be used as the driving unit 12 and a horizontal scanning circuit can be used as the readout unit 13, and any of the functions of these circuit units can be implemented by using a shift register, a decoder, and the like.

The control unit 14 is configured to be able to control each element in the radiation imaging apparatus 1, and the functions of the control unit can be implemented by an ASIC in this embodiment. However, in a similar manner to the arithmetic processing apparatus 4, the control unit can be implemented by either hardware or software.

For example, the control unit 14 can control the driving operation of the sensor array 11 by supplying a predetermined control signal (a start pulse signal, a clock signal, or the like) to the driving unit 12. The control unit 14 also performs signal readout from the sensor array 11 by supplying another control signal (a start pulse signal, a clock signal, or the like) to the readout unit 13. In this point of view, it can be said that the control unit 14 has a function as a timing generator. The control unit 14 also receives sensor signals that have been read out from the plurality of the sensor units S of the sensor array 11 by the readout unit 13, and generates image data by performing AD conversion on the received sensor signals. In this point of view, it can be said that the control unit 14 also has a function as a processor.

Although the control unit 14 has been shown as a single element in this embodiment, the control unit 14 may be formed by two or more elements and, for example, some of the above-described functions may be implemented by separate elements. Also, some of the functions of the control unit 14 may be arranged in the arithmetic processing apparatus 4, and the control unit 14 may include some of the functions of the arithmetic processing apparatus 4. Although details will be described later, the arithmetic processing apparatus 4 or the control unit 14 can perform arithmetic processing based on an energy subtraction method by using the image data which is based on the sensor signals from the sensor array 11.

The power supply unit 15 generates corresponding electrical power based on external power supply and supplies the generated power so that each element in the radiation imaging apparatus 1 can operate appropriately. For example, the power supply unit 15 supplies a power supply voltage, a ground voltage, and the like to each sensor unit S of the sensor array 11. A power supply IC that includes, for example, an AC/DC converter, a DC/DC converter, or the like can be used in the power supply unit 15.

Figure 2:
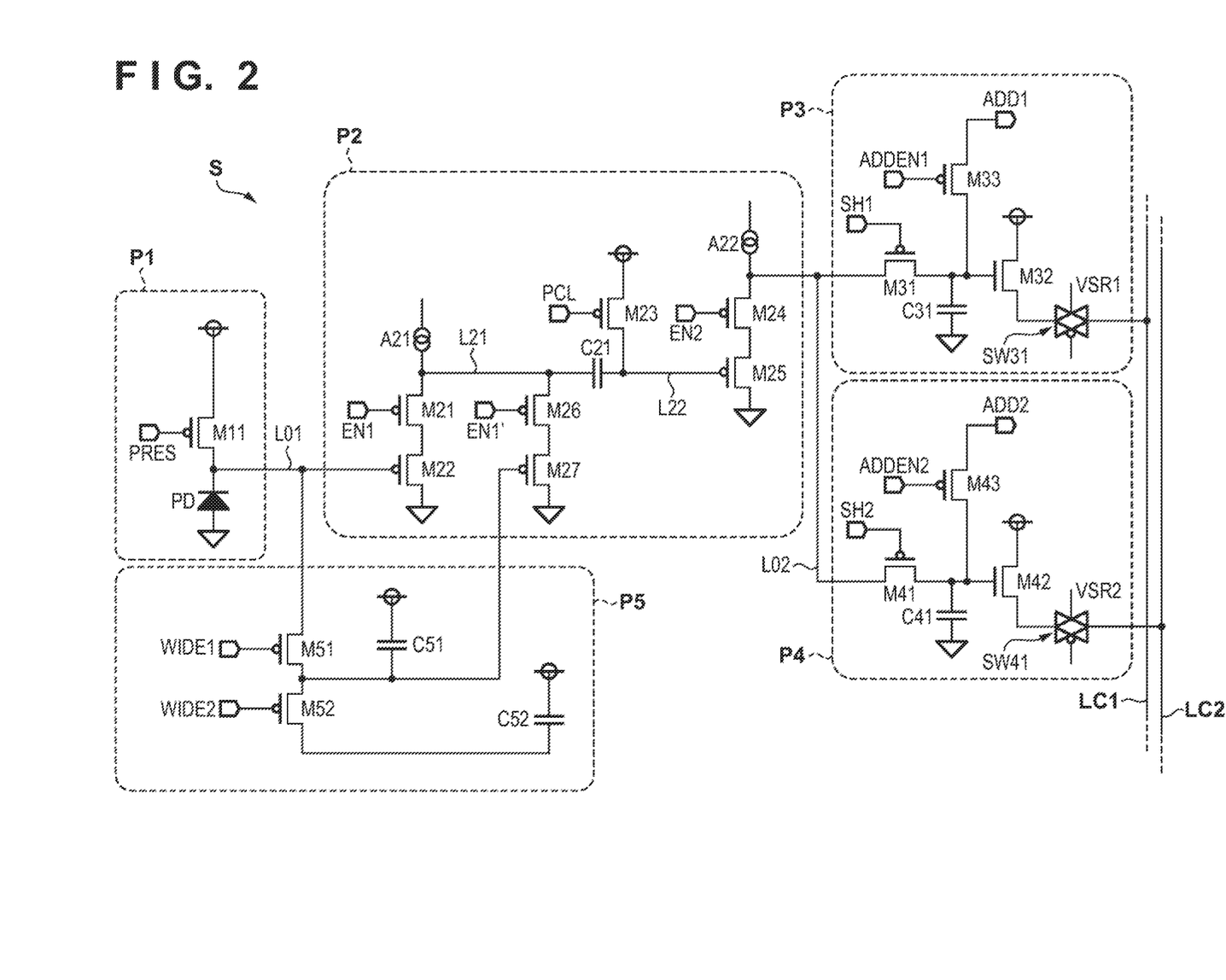
FIG. 2 is a circuit diagram showing an example of the arrangement of a sensor unit.

FIG. 2 shows an example of the arrangement of each of the plurality of sensor units S of the sensor array 11. Although a description that is focused on the arrangement of a given individual sensor unit S will be given below, a similar description is also applicable to the other sensor units S. In this embodiment, the sensor unit S includes a radiation detection unit P1, a signal amplification unit P2, a first sampling unit P3, a second sampling unit P4, and a dynamic range expansion unit P5.

The radiation detection unit P1 includes a detection element PD and a transistor M11. The signal amplification unit P2 includes transistors M21 to M27, a capacitor C21, and current sources A21 and A22. The first sampling unit P3 includes transistors M31 to M33, a capacitor C31, and an analog switch SW31. The second sampling unit P4 includes transistors M41 to M43, a capacitor C41, and an analog switch SW41. The dynamic range expansion unit P5 includes transistors M51 and M52 and capacitors C51 and C52.

Although MOS transistors are used as the transistor M11 and the like in this embodiment, other switch elements such as bipolar transistors, junction transistors, and the like may be used as another embodiment. In this embodiment, as shown in FIG. 2, n-channel MOS transistors are used as the transistors M32 and M42, and p-channel MOS transistors are used as the other transistors M11 and the like. Although a switch element obtained by connecting an n-channel MOS transistor and a p-channel MOS transistor in parallel is used as each of the analog switches SW31 and SW41, the present invention is not limited to this.

In the radiation detection unit P1, the detection element PD and the transistor M11 are connected in series so as to form a current path between a power supply line and a ground line. As each detection element PD in the indirect conversion method sensor array 11 according to this embodiment, a photoelectric conversion element such as a photodiode or the like is used as an element for detecting radiation. The detection element PD is connected to the ground line by an anode. The source terminal of the transistor M11 is connected to the power supply line, and the drain terminal is connected to the cathode of the detection element PD. A control signal PRES is input to the gate terminal of the transistor M11, and this control signal PRES can be used to control (can be used to perform control to set a conductive state or a non-conductive state in) the transistor M11. A signal line L01 is a signal line connected to a node between the detection element PD and the transistor M11.

In the signal amplification unit P2, the current source A21 and the transistors M21 and M22 are connected in series so as to form a current path between the power supply line and the ground line. More specifically, the source terminal of the transistor M21 is connected to the current source A21, and the drain terminal is connected to the source terminal of the transistor M22. The drain terminal of the transistor M22 is connected to the ground line. A control signal EN1 is input to the gate terminal of the transistor M21, and the transistor M21 can be controlled by this control signal EN1. A signal line L21 is a signal line connected to a node between the current source A21 and the transistor M21.

The current source A22 and the transistors M24 and M25 are connected in series so as to form a current path between the power supply line and the ground line. More specifically, the source terminal of the transistor M24 is connected to the current source A22, and the drain terminal is connected to the source terminal of the transistor M25. The drain terminal of the transistor M25 is connected to the ground line. A control signal EN2 is input to the gate terminal of the transistor M24, and the transistor M24 can be controlled by this control signal EN2. Also, a signal line L22 is a signal line connected to the gate terminal of the transistor M25. The capacitor C21 is connected between the signal lines L21 and L22. Also, a signal line L02 is a signal line connected to a node between the current source A22 and the transistor M24.

The source terminal of the transistor M23 is connected to the power supply line, and the drain terminal is connected to the signal line L22. A control signal PCL is input to the gate terminal of the transistor M23, and the transistor M23 can be controlled by this control signal PCL.

The source terminal of the transistor M26 is connected to the signal line L21, and the drain terminal is connected to the source terminal of the transistor M27. A control signal EN1' is input to the gate terminal of the transistor M26. and the transistor M26 can be controlled by this control signal EN1'. The drain terminal of the transistor M27 is connected to the ground line.

In the first sampling unit P3, the source terminal of the transistor M31 is connected to the signal line L02. A control signal SH1 is input to the gate terminal of the transistor M31, and the transistor M31 can be controlled by the control signal SH1. One terminal of the capacitor C31 is connected to the drain terminal of the transistor M31, and the other terminal is connected to the ground line. That is, the transistor M31 is arranged so as to set a conductive state between the signal line L02 and the capacitor C31.

The drain terminal of the transistor M32 is connected to the power supply line, the source terminal is connected to the analog switch SW31, and the gate terminal is connected to the drain terminal of the transistor M31. In each column of the sensor array 11, a column signal line LC1 is arranged in common for the sensor units S belonging to the column, and the analog switch SW31 is arranged between the transistor M32 and the column signal line LC1 so as to be controllable by a control signal VSR1.

The transistor M33 is arranged so as to form a current path between the drain terminal of the transistor M31 and an output terminal ADD1. The control signal ADDEN1 is input to the gale terminal of the transistor M33, and the transistor M33 can be controlled by a control signal ADDEN1. The output terminal ADD1 is connected to the output terminal ADD1 of another adjacent sensor unit S.

The second sampling unit P4 includes a circuit arrangement similar to that of the first sampling unit P3. That is, the transistors M41 to M43, the capacitor C41, and the analog switch SW41 act in a similar manner to the transistors M31 to M33, the capacitor C31, and the analog switch SW31, respectively. The transistor M41 can be control led by a control signal SH2. In each column of the sensor array 11, a column signal line LC2 is arranged in common to the sensor units S belonging to the column in a similar manner to the column signal line LC1, and the analog switch SW41 is arranged between the transistor M42 and the column signal line LC2 so as to be controllable by a control signal VSR2. The transistor M43 can be controlled by a control signal ADDEN2, and an output terminal ADD2 is connected to the output terminal ADD2 of another adjacent sensor unit S in a similar manner to the output terminal ADD1.

In the dynamic range expansion unit P5, the drain terminal of the transistor M51 is connected to the signal line L01. One terminal of the capacitor C51 is connected to the power supply line, and the other terminal is connected to the source terminal of the transistor M51. Also, the drain terminal of the transistor M52 is connected to the source terminal of the transistor M51. One terminal of the capacitor C52 is connected to the power supply line, and the other terminal is connected to the source terminal of the transistor M52. Note that a node between the transistor M51 and the transistor M52 is connected, together with the above-described other terminal of the capacitor C51, to the gate terminal of the aforementioned transistor M27.

In this embodiment, the sensor signals generated by the sensor units S can be read out by employing a so-called non-destructive readout method by the above-described arrangement. The driving unit 12 supplies, to each sensor unit S, the above-described control signals PRES, EN1, EN1', EN2, PCL, SH1, ADDEN1, VSR1, SH2, ADDEN2, VSR2 and control signals WIDE1 and WIDE2 to drive the units P1 to P5 of each sensor unit S. The radiation detection unit P1 outputs, to the signal line L01, a signal corresponding to the radiation dose to the detection element PD, and the signal amplification unit P2 amplifies the signal of the signal line L01 and outputs the amplified signal to the signal line L02. Note that although the signal propagated through the signal line L02 corresponds to the signal from the detection element PD and is a signal amplified by the signal amplification unit P2 this embodiment, it may be the signal (the signal of a value corresponding to the amount of charges generated in the detection element PD) itself from the detection element PD in another embodiment. The first sampling unit P3 and the second sampling unit P4 are connected in common to the signal line L02, and each of the first sampling unit and the second sampling unit can sample a signal that propagates through the signal line L02. The dynamic range expansion unit P5 can expand the dynamic range (or change the sensor sensitivity) of the sensor unit S by adding capacitance to the signal line L01.

The control signals ADDEN1 and ADDEN2 are used to perform averaging (perform so-called binning) of sensor signals between two (or two or more) sensor units S which are adjacent to each other. However, assume that binning will not be performed in this case for the sake of descriptive convenience hereinafter. That is, assume that the control signals ADDEN1 and ADDEN2 will be maintained at an inactive level (H (High) level in this embodiment).

Also, although the control sisals WIDE1 and WIDE2 are used to expand the dynamic range of the sensor unit S, assume that the dynamic range of the sensor unit S will not be expanded in this case for the sake of descriptive convenience hereinafter. That is, assume that the control signals WIDE1 and WIDE2 will be maintained at an inactive level. Also, in a case in which the sensor signals are to be read out without expanding the dynamic range of the sensor unit S, the control signal EN1 will be maintained at an active level (an L (Low) level in this embodiment) and the control signal EN1' will be maintained at an inactive level.

The general outline of the driving method of the sensor unit S when radiation imaging is to be performed is as follows. First, the sensor units S are reset, and sampling and outputting of the sensor signals are performed subsequently in response to the start of radiation irradiation. In this embodiment a plurality of sampling operations are performed by using the first sampling unit P3 and the second sampling unit P4 during or after a radiation irradiation operation performed in a predetermined period. For example, a sensor signal sampled by the first sampling unit P3 is held in the first sampling unit P3 while the transistor M31 is maintained in a non-conductive state. Hence, this sensor signal can be read out from the first sampling unit P3 at an arbitrary timing during this period, that is, can be read out by the non-destructive readout method. This is also applicable to the second sampling unit P4.

Figure 3:
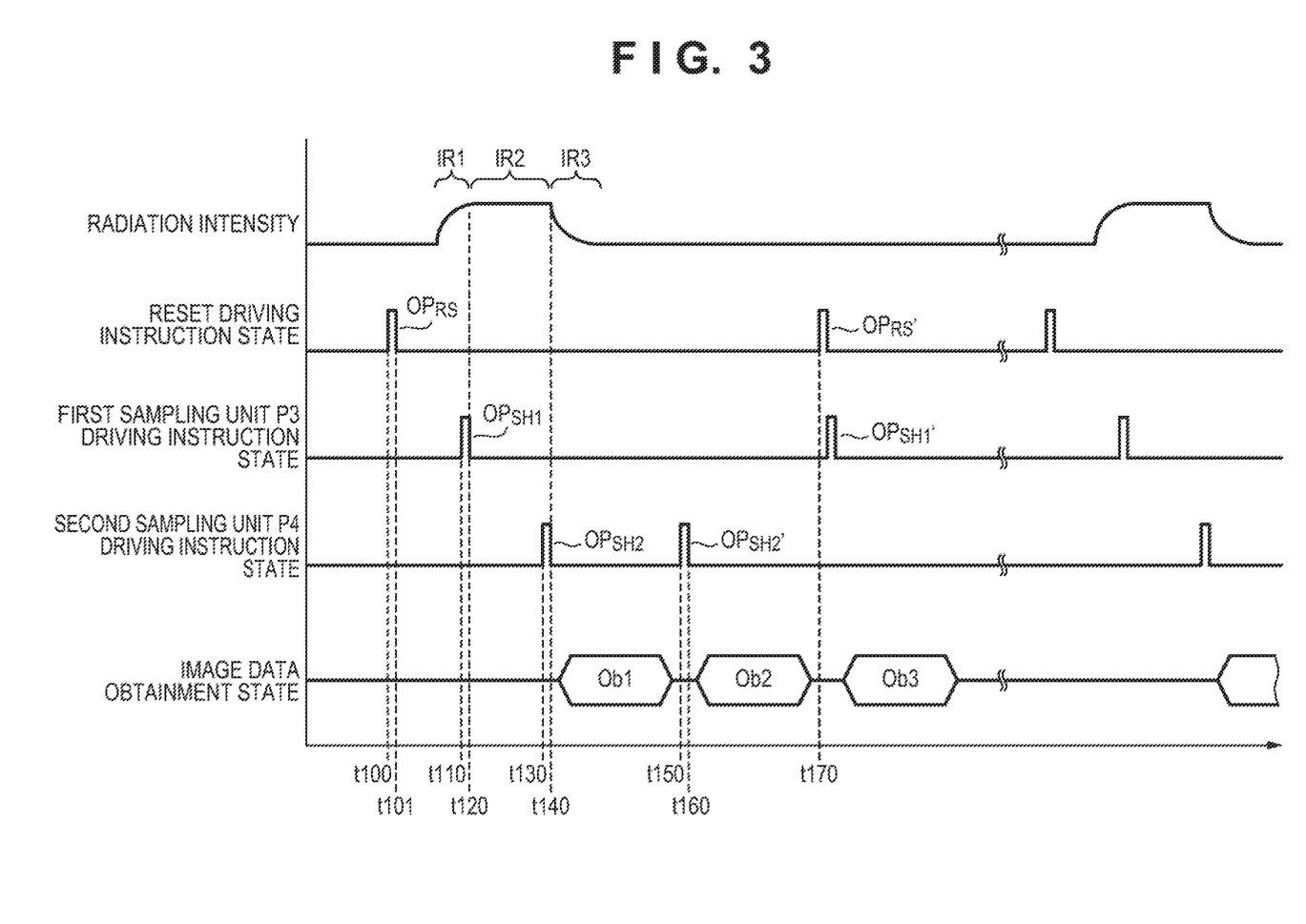
FIG. 3 is a timing chart showing a reference example of a driving method of the radiation imaging apparatus.

FIG. 3 is a timing chart showing an example of the driving method of the above-described sensor unit S. Assume that a time axis is indicated on the abscissa of FIG. 3. The radiation intensity, the reset driving instruction state, the driving instruction state of the first sampling unit P3, the driving instruction state of the second sampling unit P4, and the image data obtainment state are indicated on the ordinate of FIG. 3.

"Radiation Intensity" of FIG. 3 indicates the radiation dose generated by the radiation source 2 per unit time. As described above, the radiation source 2 is configured to chronologically change the radiation intensity. In this case, the radiation imaging apparatus 1 will receive the information indicating the mode of change of the radiation intensity from the arithmetic processing apparatus 4 before or during the radiation irradiation operation.

"Reset Driving Instruction State" of FIG. 3 indicates the presence absence of an instruction to execute resetting of the sensor unit S. For example, when the reset driving instruction state shifts from the L level to the H level, resetting (a react driving operation $OP_{RS}$) of each clement of the sensor unit S is executed. Referring to FIG. 2, it can be seen that the potential of each node in the sensor unit S is initialized by setting the control signals PRES, EN1, EN2, PCL, SH1, and SH2 at the active level by performing this reset driving operation $OP_{RS}$. For example, setting the control signal PRES to the active level sets the transistor M11 in a conductive state, thereby removing the charges of the detection element PD and initializing the potential of the signal line L01. The potentials of the other signal lines L02, L21, and L22 are also initialized in a similar manner.

Note that in a case in which the dynamic range of the sensor unit S is to lie expanded, the control signals EN1', WIDE1, and WIDE2 can also be set to the active level in the above-described reset driving operation $OP_{RS}$. Also, in a case in which the aforementioned binning Is to be performed, the control signals ADDEN1 and ADDEN2 can be further set to the active level in the above-described reset driving operation $OP_{RS}$.

Subsequently, when the reset driving instruction state shifts from the H level to the L level, the control signals PRES, PCL, SH1, and SH2 are set to the inactive state to complete the reset driving operation $OP_{RS}$. At this time, a noise component (or an offset component), at the time of the reset operation, which is also referred to as kTC noise or the like will be clamped by the capacitor C21.

Note that by setting the control signal EN1 to the active level after the above-described reset driving operation $OP_{RS}$, the transistor M21 will be set to the conductive state, and the transistor M22 will therefore perform a source follower operation. As a result, when radiation irradiation is started, a signal corresponding to the amount of change of the gate potential of the transistor M22 will propagate to the signal line L21 and subsequently propagate to the signal line L22 via the capacitor C21. Also, by setting the control signal EN2 to the active level, the transistor M24 will be set to the conductive state, and the transistor M25 will therefore perform a source follower operation. As a result, the signal propagating through the above-described signal line L22 will propagate to the signal line L02.

"Driving Instruction State of First Sampling Unit P3" of FIG. 3 indicates the presence absence of an instruction to cause the first sampling unit P3 to execute sampling of a signal propagating through the signal line L02. For example, when the driving instruction state of the first sampling unit P3 shifts from the L level to the H level, the first sampling unit P3 will start sampling (a first sampling driving operation $OP_{SH1}$ of) the signal propagating through the signal line L02. Referring to FIG. 2, it can be seen that the control signal SH1 corresponds to the first driving signal for driving the first sampling unit P3 in the first sampling driving operation $OP_{SH1}$. By setting the control signal SH1 to the active level, the transistor M31 is set to the conductive state, and the capacitor C31 will be set to a voltage corresponding to the signal propagating through the signal line L02. Subsequently, when the driving instruction state of the first sampling unit P3 shifts from the H level to the L level, the voltage of the capacitor C31 will be held by setting the control signal SHI to the inactive level, thereby completing the first sampling driving operation $OP_{SH1}$. The above-described voltage held by the capacitor C31 can be read out, via the column signal line LC1, as a sensor signal sampled by the first sampling driving operation $OP_{SH1}$ by setting the analog switch SW31 in the conductive state. More specifically, the voltage of the source terminal changes in accordance with the voltage of the gate terminal (the voltage of the capacitor C31) by the source follower operation of the transistor M32. The analog switch SW31 outputs, as the sensor signal to the column signal line LC1, the signal corresponding to the voltage of this source terminal.

"Driving Instruction State of Second Sampling Unit P4" of FIG. 3 indicates, in a similar manner to the above-described "Driving Instruction State of First Sampling Unit P3", the presence absence of an instruction to cause the second sampling unit P4 to execute sampling of a signal propagating through the signal line L02. For example, in a case in which the driving instruction state of the second sampling unit P4 shifts from the L level to the H level, the second sampling unit P4 will start sampling (a second sampling driving operation $OP_{SH2}$ of) the signal propagating through the signal line L02. Referring to FIG. 2, it can be seen that the control signal SH2 corresponds to the second driving signal for driving the second sampling unit P4 in the second sampling driving operation $OP_{SH2}$. By setting the control signal SH2 to the active level, the transistor M41 is set to the conductive state, and the capacitor C41 will be set to a voltage corresponding to the signal propagating through the signal line L02. Subsequently, when the driving instruction slate of the second sampling unit P4 shifts from the H level to the L level, the voltage of the capacitor C41 will be held by setting the control signal SH2 to the inactive level, thereby completing the second sampling driving operation $OP_{SH2}$. The above-described voltage held by the capacitor C41 can be read out, via the column signal line LC2, as a sensor signal sampled by the second sampling driving operation $OP_{SH2}$ by setting the analog switch SW41 in the conductive state.

The reset driving instruction, the driving instruction state of the first sampling unit P3, and the driving instruction state of the second sampling unit P4 described above are supplied from the arithmetic processing apparatus 4 to the radiation imaging apparatus 1 in the example of FIG. 2. As described above, the radiation imaging apparatus 1 receives, from the arithmetic processing apparatus 4, information indicating the mode of change of the radiation intensity. In this example, the reset driving instruction, the driving instruction state of the first sampling unit P3, and the driving instruction of the second sampling unit P4 may be supplied as this information from the arithmetic processing apparatus 4.

"Image Data Obtainment State" of FIG. 3 indicates whether image data based on the sensor signals sampled by the above described first sampling driving operation $OP_{SH1}$ and the second sampling driving operation $OP_{SH2}$ is to be obtained. Although details will be described later, assume that the image data obtainment will be performed three tines (to be referred to as obtainment operations Ob1, Ob2, and Ob3, respectively) in this case.

Referring to FIG. 3, the reset driving instruction state shifts to the H level and the reset driving operation $OP_{RS}$ is started at time t100, and the reset driving instruction state shifts to the L level and the reset driving operation $OP_{RS}$ is subsequently completed at time t101. As a result, the potential of each node in the sensor unit S is initialized, and, for example, the potentials of the signal line L01 and the L02 are initialized.

After the reset driving operation $OP_{RS}$ is completed at time t101, the radiation irradiation to the sensor array 11 is started. As described above, the radiation intensity changes chronologically, and changes so as to be held at a constant level over a predetermined period after increasing gradually, and to further gradually decrease thereafter as shown in FIG. 3. Assume that a dose IR1 is the radiation dose during the period when the radiation intensity is increasing, a dose IR2 is the radiation dose during a period in which the radiation intensity is set to a constant level, and a dose IR3 is the radiation dose during a period in which the radiation intensity is decreasing.

To obtain a sensor signal corresponding to the dose IR1, the driving instruction state of the first sampling unit P3 shifts to the H level at time t110, and the first sampling driving operation $OP_{SH1}$ is started. As is obvious from FIG. 2, charging of the capacitor C31 is started at the timing in which the transistor M31 is set to the conductive state in the first sampling unit P3. Hence, time t110 corresponds to the start liming of the first sampling driving operation $OP_{SH1}$.

Subsequently, at time t120. the driving instruction slate of the first sampling unit P3 shifts to the L level, and the first sampling driving operation $OP_{SH1}$ is completed. As is obvious from FIG. 2, in the first sampling unit P3, the voltage of the capacitor C31 is confirmed at the timing in which the transistor M31 is set to the nonconductive state. Hence, time t120 corresponds to the completion timing of the first sampling driving operation $OP_{SH1}$. In this manner, the sensor signal corresponding to the dose IR1 is sampled by the first sampling unit P3.

Subsequently, to further obtain sensor signals corresponding to the doses IR1 and IR2, the second sampling driving operation $OP_{SH2}$ is performed from time t130 to time t140 in a similar manner to the first sampling driving operation $OP_{SH1}$ performed from time t110 to time t120. More specifically, at time t130, the driving instruction state of the second sampling unit P4 shifts to the H level, and the second sampling driving operation $OP_{SH2}$ is started. Subsequently, at time t140, the driving instruction state of the second sampling unit P4 shifts to the L level, and the second sampling driving operation $OP_{SH2}$ is completed. Time t130 corresponds to the start timing of the second sampling driving operation $OP_{SH2}$, and time t140 corresponds to the completion timing of the second sampling driving operation $OP_{SH2}$. In this manner, the sensor signals corresponding to the doses IR1 and IR2 are sampled by the second sampling unit P4.

From time t140 and onward, the radiation intensity decreases and substantially becomes zero, thereby ending the processing corresponding to a single radiation irradiation operation. Also, the obtainment operation Ob1 of image data will be performed from time t140 and onward which is after the completion of the second sampling driving operation $OP_{SH2}$.

First, the analog switch SW31 of the first sampling unit P3 of each of the plurality of sensor units S is set to the conductive state to read out the sensor signals by the readout unit 13, and image data is generated based on the sensor signals read out in this manner. Each of the sensor signals forming this image data includes a signal component based on the dose IR1 and an incident noise component (a component corresponding to a noise component at the time of the reset operation or an offset component). This image data will be referred to as image data D(IR1).

Next, the analog switch SW41 of the second sampling unit P4 of each of the plurality of sensor units S is set to the conductive state to read out the sensor signals by the readout unit 13, and image data is generated based on the sensor signals read out in this manner. Each of the sensor signals forming this image data includes a signal component based on the doses IR1 and IR2 and an incident noise component. This image dam will be referred to as image data D(IR1+IR2).

Subtraction processing of the image data D(IR1) and the image data D(IR1+IR2) obtained in this manner is performed. As a result, image data formed by the sensor signals each including a signal component based on the dose IR2 is generated as image data $D_{CR}(IR2)$.

Subsequently, another second sampling driving operation (to be denoted as "$OP_{SH2}$" for the sake of discrimination) is performed from time t150 to time t160 to obtain sensor signals corresponding to the doses IR1 to IR3. This second sampling driving operation $OP_{SH1}$ can be performed in a similar manner to the first sampling driving operation $OP_{SH2}$ and the like performed from time t110 to time t120. In this second sampling driving operation $OP_{SH2}'$, the sensor signals (the sensor signals corresponding to the doses IR1 and IR2) sampled in the second sampling driving operation $OP_{SH2}$ are overwritten by the sensor signals corresponding to the doses IR1 to IR3.

The obtainment operation Ob2 of image data is performed after the completion of the second sampling driving operation $OP_{SH2}'$ from time t160 and onward. In this case, the analog switch SW41 of the second sampling unit P4 of each of the plurality of sensor units S is set to the conductive state to read out the sensor signals by the readout unit 13, and image data is generated based on the sensor signals read out in this manner. Each of the sensor signals forming this image data includes a signal component based on the doses IR1, IR2, and IR3 and an incident noise component. This image data will be referred to as image data D(IR1+IR2+IR3).

The subtraction processing of the aforementioned image data D(IR1) and the image data D(IR1+IR2+IR3) obtained in this manner is performed. As a result, image data formed by sensor signals each including a signal component based on the doses IR2 and IR3 is generated as image data $D_{CR}(IR2+IR3)$. The subtraction processing of the aforementioned image data $D_{CR}(IR2)$ and this image data $D_{CR}(IR2+IR3)$ is also performed. As a result, image data formed by sensor signals each including a signal component based on the dose IR3 is generated as image data $D_{CR}(IR3)$.

Subsequently, from time t170 and onward, another reset driving operation (to be denoted as "$OP_{RS}'$" for the sake of discrimination) and another first sampling driving operation (to be denoted as "$OP_{SH1}'$" for the sake of discrimination) are sequentially performed. This reset driving operation $OP_{RS}'$ can be performed in a similar manner to the reset driving operation $OP_{RS}$ performed from time t100 to time t101. Also, this first sampling driving operation $OP_{SH1}'$ can be performed in a similar manner to the first sampling driving operation $OP_{SH1}$ performed from time t110 to time t120. In this first sampling driving operation $OP_{SH1}'$, each of the sensor signals (sensor signals corresponding to the dose IR1) which were sampled in the first sampling driving operation $OP_{SH1}$ is overwritten to be the signal value (a value which does not substantially include the signal component) after the reset driving operation $OP_{RS}'$.

Subsequently, the obtain men t operation Ob3 of the image data is performed. The analog switch SW31 of the first sampling unit P3 of each of the plurality of sensor units S is set to the conductive state to read out the sensor signals by the readout unit 13, and image data is generated based on the sensor signals read out in this manner. Each of the sensor signals forming this image data substantially includes only the noise component. This image data will be referred to as image data D(dark). This image data D(dark) may also be referred to as dark image data or the like.

The subtraction processing of the aforementioned image data D(IR1+IR2+IR3) and the image data D(dark) obtained in this manner is performed. As a result, image data formed by sensor signals each including a signal component based on the doses IR1, IR2, and IR3 is generated as image data $D_{CR}(IR1+IR2+IR3)$. The subtraction processing of the aforementioned image data $D_{CR}(IR2+IR3)$ and this image data $D_{CR}(IR1+IR2+IR3)$ is also performed. As a result, image data formed by sensor signals each including a signal component based on the dose IR1 is generated as image data $D_{CR}(IR1)$.

Note that the various kinds of image data described above can be sorted as follows:

Image data D(IR1)
... image data including the signal component and the noise component of the dose IR1

Image data D(IR1+IR2)
... image data including the signal component and the noise component of the doses IR1 and IR2

Image data D(IR1+IR2+IR3)
... image data including the signal component and the noise component of the doses IR1, IR2, and IR3

Image data $D_{CR}(IR2+IR3)$
... image data substantially including only the signal component of the doses IR2 and IR3

Image data $D_{CR}(IR1+IR2+IR3)$
... image data substantially including only the signal component of the doses IR1, IR2, and IR3

Image data $D_{CR}(IR1)$
... image data substantially including only the signal component of the dose IR1

Image data $D_{CR}(IR2)$
... image data substantially including only the signal component of the dose IR2

Image data $D_{CR}(IR3)$
... image data substantially including only the signal component of the dose IR3

Image data L(dark)
... image data substantially including only the noise component.

Since the image data $D_{CR}(IR1)$, $D_{CR}(IR2)$, and $D_{CR}(IR3)$ obtained as described above are image data obtained under mutually different radiation intensities, it will be possible to observe various kinds of radiation images by employing the energy subtraction method using these image data. For example, various kinds of radiation images such as an image of a bone tissue, an image of a soft tissue, images using a contrast agent, and the like of the subject can be observed by adding and subtracting any two sets of data selected from the image data $D_{CR}(IR1)$, $D_{CR}(IR2)$, and $D_{CR}(IR3)$.

Note that although an example of a mode in which the first sampling driving operation $OP_{SH1}$ is performed by using the first sampling unit P3 and the second sampling driving operation $OP_{SH2}$ is subsequently performed by using the second sampling unit P4 has been described here, the order of the units may be reversed. For example, as another mode, the second sampling unit P4 may be used to perform sampling as the first sampling driving operation $OP_{SH1}$ and the first sampling unit P3 may be used to perform sampling as the second sampling driving operation $OP_{SH2}$.

The first sampling unit P3 and the second sampling unit P4 are formed so as to have similar sampling characteristics and similar sampling accuracies. That is, mutually similar parameters are applied to elements such as the transistors, the capacitors, and the like forming the first sampling unit P3 and the second sampling unit P4, and more preferably, the elements are arranged so as to have symmetry by having similar structures and layouts.

However, according to the driving method of the sensor unit S according to the example of FIG. 3, the sampling characteristic of the first sampling driving operation $OP_{SH1}$ may become different from that of the second sampling driving operation $OP_{SH2}$ in some cases. This is thought to be caused when the sampling characteristic of the first sampling unit P3 is influenced by an unexpected parasitic capacitance (floating capacitance) when the first sampling unit P3 is driven in the first sampling driving operation $OP_{SH1}$. For example, when the transistor M31 is set in the conductive state by setting the control signal SH1 to the active level, charges may flow from the parasitic capacitance into the capacitor C31 or charges may flow out from the capacitor 31 to the parasitic capacitance. The occurrence of these influences is equivalent to a state in which an unexpected component becomes mixed into a signal to be sampled by the first sampling unit P3, thus causing unexpected change in the sampling characteristic, leading to sampling accuracy degradation, and further causing degradation of the quality of the radiation image.

Note that the above-described parasitic capacitance is formed between the first sampling unit P3 and at least one of the other units P1, P2, P4, and P5, and is caused by the circuit arrangement, the structure, the layout, and the like of the sensor unit S. Also, the unexpected change in the sampling characteristic described above can occur in a similar manner in the second sampling unit P4 in a case in which the first sampling driving operation $OP_{SH1}$ is to be performed by using the second sampling unit P4 as another embodiment.

Figure 4:
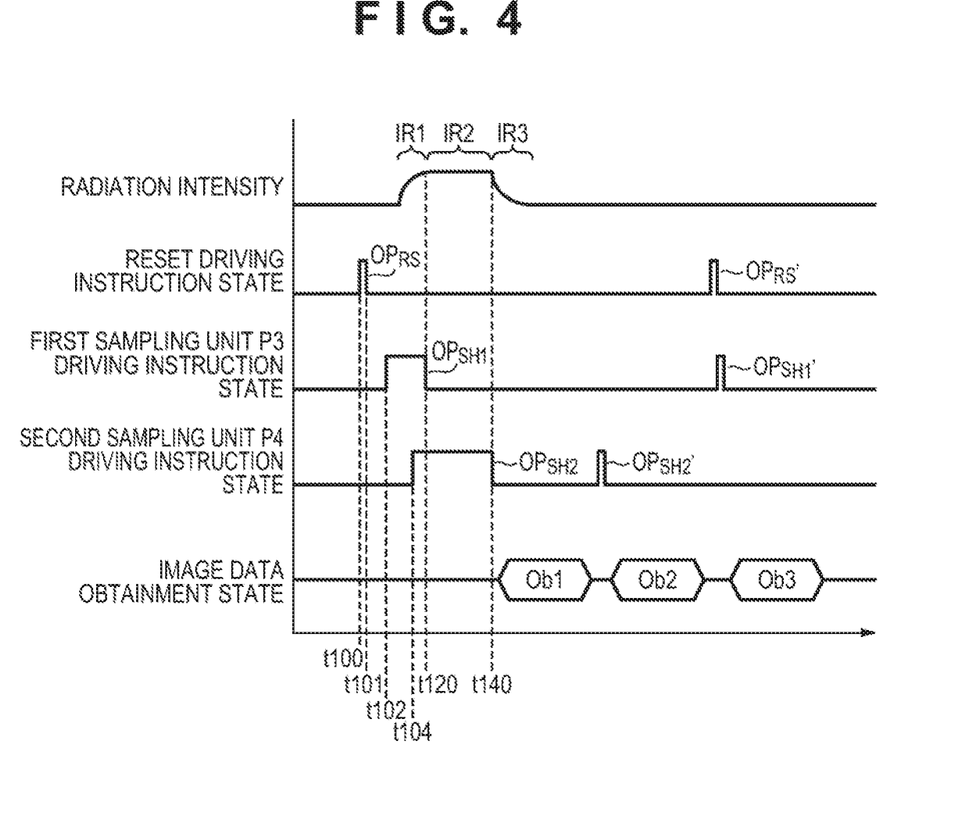
FIG. 4 is a timing chart showing an example of the driving method of the radiation imaging apparatus.

A driving method that can reduce such unexpected changes in the sampling characteristic will be described hereinafter with reference to FIG. 4. FIG. 4 shows, in a similar manner to FIG. 3 (reference example), a timing chart showing a driving method of the sensor unit S according to this embodiment.

In this embodiment, as shown in FIG. 4, the first sampling driving operation $OP_{SH1}$ is started at time t102 after the completion of the reset driving operation $OP_{SH2}$ and is completed at time t120. More specifically, the control signal SH1 is activated at time t102, and the control signal SH1 is inactivated at time t120. On the other hand, the second sampling driving operation $OP_{SH2}$ is started at time t104 before the completion of the first sampling driving operation $OP_{SH1}$, and is completed at time t140. More specifically, the control signal SH2 is activated at time t104, and the control signal SH2 is inactivated at time t140. In this embodiment, the timing (time t104) at which the control signal SH2 is set to the active level is after the timing (time t102) at which the control signal SH1 is set to the active level and is before the timing (time t120) at which the control signal SH1 is set to the inactive level.

According to such a driving method, the period (time t102 to time t120) in which the control signal SH1 is maintained at the active level will partially overlap the period (time t104 to time t140) in which the control signal SH2 is maintained at the active level. A state in which both the first sampling unit P3 and the second sampling unit P4 are being driven will be set during the period from time t104 to time t120. As a result, the unexpected component that can mix into the first sampling unit P3 during the first sampling driving operation $OP_{SH1}$ can be mitigated, and the aforementioned unexpected change in the sampling characteristic of the first sampling unit P3 can be reduced or suppressed. Hence, the first sampling driving operation $OP_{SH1}$ can be appropriately implemented under a desired sampling characteristic without the sampling characteristic of the first sampling unit P3 changing unexpectedly.

Note that other driving operations such as the driving operations $OP_{RS}'$, $OP_{SH1}'$, and $OP_{SH2}'$ according to this embodiment will be performed in a similar manner to those of FIG. 3 (reference example), and a description thereof will be omitted.

As described above, in this embodiment, the driving unit 12 will perform the reset driving operation $OP_{RS}$ from time t100 to time t101 before the start of radiation irradiation on the sensor array 11. Also, from time t102 to time t120 which is after the completion of the reset driving operation $OP_{RS}$ and before the start of the radiation irradiation, the driving unit 12 will use the first sampling unit P3 to perform the first sampling driving operation $OP_{SH1}$ to sample each signal propagating through the signal line L02. Furthermore, from time t104 to time t140, the driving unit 12 will use the second sampling unit P4 to perform the second sampling driving operation $OP_{SH2}$ to sample each signal propagating through the signal line L02.

The driving unit 12 will start the second sampling driving operation $OP_{SH2}$ before the completion of the first sampling driving operation $OP_{SH1}$, and complete the second sampling driving operation $OP_{SH2}$ after the completion of the first sampling driving operation $OP_{SH1}$. According to such a driving method, the aforementioned unexpected change in the sampling characteristic that can occur in the first sampling unit P3 can be reduced because the unexpected component that can mix into the first sampling unit P3 during the first sampling driving operation $OP_{SH1}$ can be mitigated. Hence, the first sampling driving operation $OP_{SH1}$ can be implemented appropriately under a desired sampling characteristic. Therefore, according to this embodiment, the sampling characteristics of a plurality of sampling operations (the sampling driving operations $OP_{SH1}$, $OP_{SH2}$, and the like) can be averaged, and the sampling accuracy of the sensor signals can be improved.

Note that the value of each sensor signal that is sampled by the first sampling unit P3 is confirmed at the completion timing of the first sampling driving operation $OP_{SH1}$. Thus, the start timing of the first sampling driving operation $OP_{SH1}$ suffices to be later than the time t101 which is the completion timing of the reset driving operation $OP_{RS}$ and is not limited to that of the mode according to this embodiment.

Figure 5A:
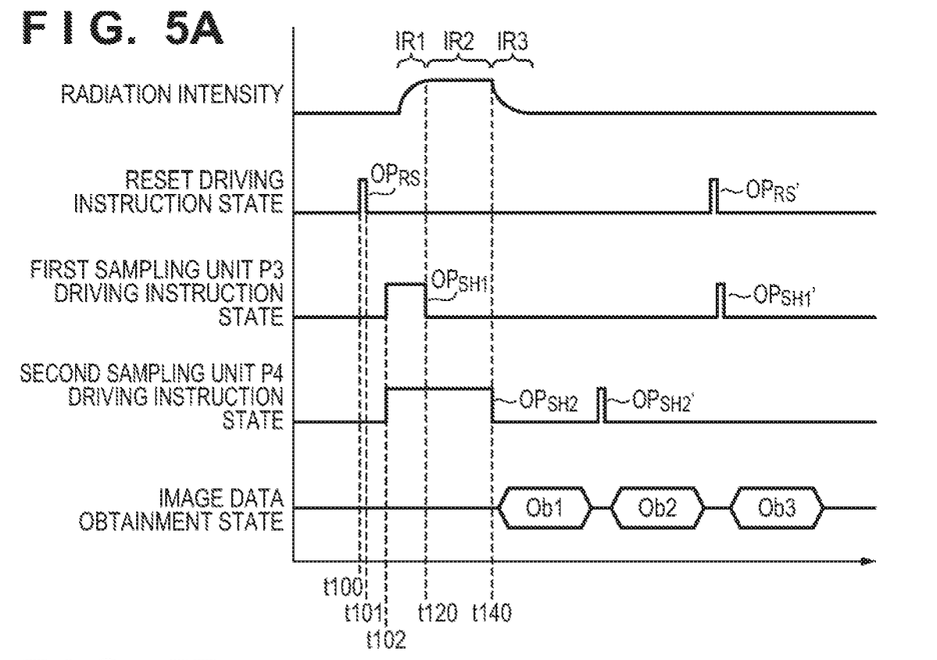
FIG. 5A is a timing chart shoving an example of the driving method of the radiation imaging apparatus.

FIG. 5A is a timing chart showing a driving method of the sensor unit S according to one mollification of the embodiment. In this example, the first sampling driving operation $OP_{SH1}$ and the second sampling driving operation $OP_{SH2}$ are started simultaneously at time t102. That is, the timing at which the control signal SH1 is set to the active level and the timing at which the control signal SH2 is set to live active level will match at time t102. In this case as well, the period (time t102 to time t120) in which the control signal SH1 is maintained at the active level and the period (time t102 to time t140) in which the control signal SH2 is maintained at the active level will overlap. Since the unexpected component that can mix into the first sampling unit P3 can be mitigated even by supplying the control signals SH1 and SH2 in accordance with this mode, the driving unit 12 will be able to perform the first sampling driving operation $OP_{SH1}$ under an appropriate sampling characteristic.

Figure 5B:
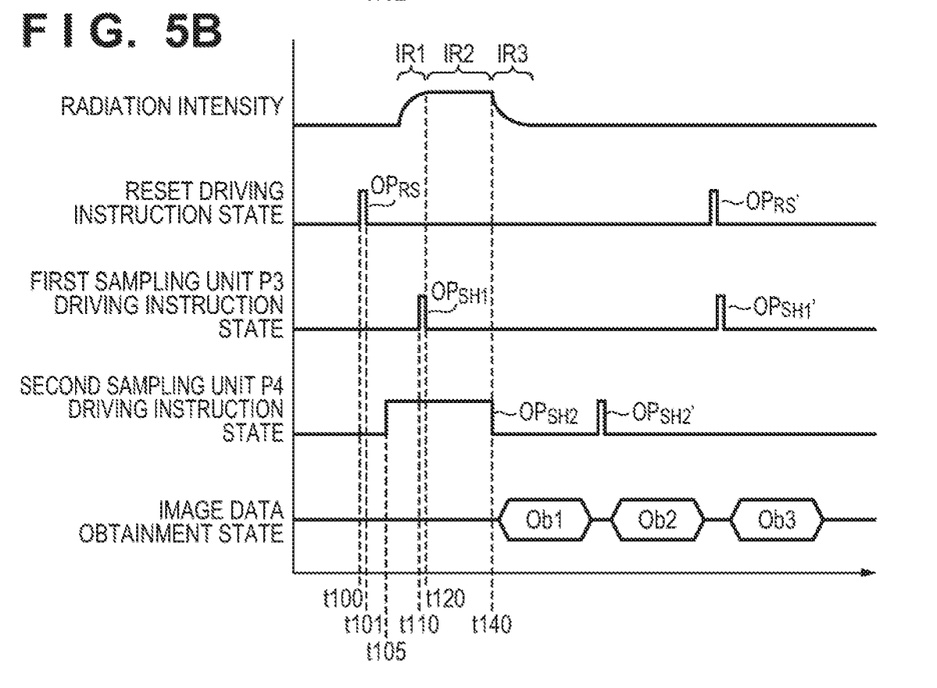
FIG. 5B is a timing chart showing an example of the driving method of the radiation imaging apparatus.

FIG. 5B is a timing chart showing a driving method of the sensor unit S according to another modification of the embodiment. In this example, the first sampling driving operation $OP_{SH1}$ is started at a timing later than the start timing of the second sampling driving operation $OP_{SH2}$. That is, the driving unit 12 sets the control signal SH2 to the active level at time t105 which is before time t110 at which the control signal SH1 is set to the active level. In this case as well the period (time t110 to time t120) in which the control signal SH1 is maintained at the active level and the period (time t105 to time t140) in which the control signal SH2 is maintained at the active level will overlap. Since the unexpected component that can mix into the first sampling unit P3 can be mitigated even by supplying the control signals SH1 and SH2 in accordance with this mode, the driving unit 12 will be able to perform the first sampling driving operation $OP_{SH1}$ under an appropriate sampling characteristic.

Although a case in which the sensor unit S includes two sampling units P3 and P4 has been exemplified in the above-described embodiment for the sake of descriptive convenience, the number of sampling units is not limited to this and may be two or more. For example, in an arrangement in which the sensor unit S includes two or more sampling units, the driving operation of another sampling unit which is different from the sampling unit related to the first sampling driving operation can be started before the first sampling driving operation is completed after the reset driving operation $OP_{RS}$. Also, in an arrangement in which the sensor unit S includes three or more sampling units, the driving operation of some of the other sampling units which are different from the sampling unit related to the first sampling driving operation may be started or the driving operation of all of the sampling units may be started.

In addition, although the sampling units P3 and P4 were discriminated and described as separate elements for the sake of descriptive convenience in the above-described embodiment, these sampling units need not be arranged individually so as to allow discrimination and may be formed by a single element. That is, as an alternative to the sampling units P3 and P4, a single sampling unit that can independently execute the first sampling driving operation $OP_{SH1}$ and the second sampling driving operation $OP_{SH2}$ may be arranged in each sensor unit S. This sampling unit may be configured to be able to execute, at least, a plurality of sampling driving operations in parallel. By using such a sampling unit, for example, it will be possible to execute two sampling driving operations at different timings from each other, and these two sampling driving operations can be set as the first sampling driving operation $OP_{SH1}$ and the second sampling driving operation $OP_{SH2}$, respectively. Hence, the driving unit 12 can also use the above-described sampling unit to perform the first sampling driving operation $OP_{SH1}$ and the second sampling driving operation $OP_{SH2}$ to sample each signal propagating through the signal line L02. Also, the driving unit 12 can start the second sampling driving operation $OP_{SH2}$ before the completion of the first sampling driving operation $OP_{SH1}$ and complete the second sampling driving operation $OP_{SH2}$ after the completion of the first sampling driving operation $OP_{SH1}$.

In addition, according to the above-described embodiment, the radiation imaging apparatus 1 receives information indicating the mode of change of the radiation intensity from the arithmetic processing apparatus 4. In this case, the mode of change of the radiation intensity can be set in advance in one of the radiation source 2, the radiation control unit 3, and the arithmetic processing apparatus 4. As another mode, the mode of change of the radiation intensity can be set in advance in the radiation imaging apparatus 1 itself. In this case, the radiation imaging apparatus 1 can determine the start end timings of each of the above-described driving operations $OP_{RS}$, $OP_{SH1}$, $OP_{SH2}$, and the like by (for example, the control unit 14 of) the self-apparatus 1.

Second Embodiment

In the above-described first embodiment, a first sampling driving operation $OP_{SH1}$ and a second sampling driving operation $OP_{SH2}$ ware performed so that a period in which a control signal SH1 is maintained at an active level and a period in which a control signal SH2 is maintained at an active level will overlap. However, as described above, an unexpected change of the sampling characteristic of a first sampling unit P3 can be reduced by mitigating an unexpected component that can mix into the first sampling unit P3. Hence, the driving operation of a second sampling unit P4 need only be started before the completion of the first sampling driving operation $OP_{SH1}$, and the second sampling driving operation $OP_{SH2}$ need not be continuously executed over a predetermined period.

Figure 6A:
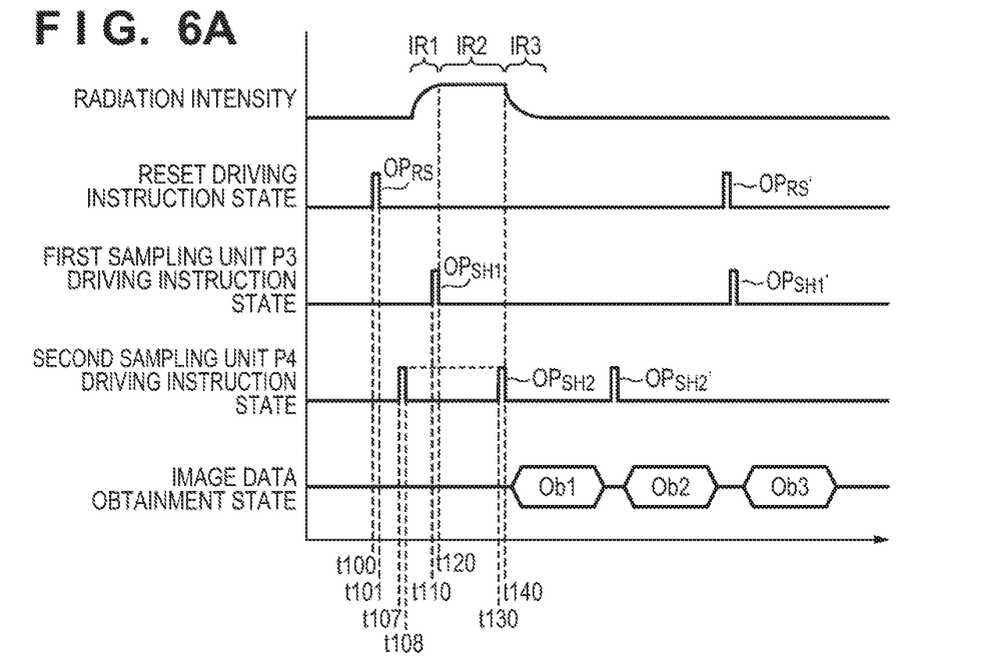
FIG. 6A is a timing chart showing an example of a driving method of a radiation imaging apparatus.

FIG. 6A is a timing chart showing an example of a driving method of a sensor unit S according to the second embodiment. In this example, after the second sampling driving operation $OP_{SH2}$ has been started at time t107 after the completion of a reset driving operation $OP_{RS}$, the second sampling driving operation $OP_{SH2}$ is suspended at time t108 before the start of the first sampling driving operation $OP_{SH1}$. Subsequently, the first sampling driving operation $OP_{SH1}$ is performed from time t110 to time t120. the second sampling driving operation $OP_{SH2}$ is restarted thereafter at time t130, and the second sampling driving operation $OP_{SH2}$ is completed at time t140.

That is, a driving unit 12 sets the control signal SH2 to the inactive level over a predetermined period from before the timing (time t110) at which the control signal SH1 is set to the active level until after the timing (time t120) at which the control signal SH1 is set to the inactive level. In this example, the second sampling driving operation $OP_{SH2}$ is suspended by maintaining the control signal SH2 at the inactive level during the period of time t108 to time t130. and the suspended second sampling driving operation $OP_{SH2}$ is restarted from time t130 and onward. Note that a state in which the second sampling driving operation $OP_{SH2}$ is being suspended is indicated by broken lines in FIG. 6A.

Although the first sampling driving operation $OP_{SH1}$ can be described in a similar manner, the start, the completion, the suspension, and the restart of the second sampling driving operation $OP_{SH2}$ according to this embodiment can be described as follows. That is, the start of the second sampling driving operation $OP_{SH2}$ indicates the first driving operation of a transistor M41 after the completion of the reset driving operation $OP_{RS}$. The completion of the second sampling driving operation $OP_{SH2}$ indicates a state in which the driving operation of the transistor M41 has been stopped and an analog switch SW41 is subsequently driven without restarting the driving operation of the transistor M41. The suspension of the second sampling driving operation $OP_{SH2}$ indicates a state in which the driving operation of the transistor M41 has been stopped and the driving operation of the transistor M41 is subsequently restarted without driving tire analog switch SW41. Also, the restart of the second sampling driving operation $OP_{SH2}$ indicates that the driving operation of the transistor M41 that has been stopped in the above-described manner is restarted.

Since the unexpected component that can mix into the first sampling unit P3 can be mitigated by also such a driving method, the first sampling driving operation $OP_{SH1}$ can be performed under an appropriate sampling characteristic.

In a similar manner to the first sampling unit P3, the value of each sensor signal sampled by the second sampling unit P4 is confirmed at the completion timing of the second sampling driving operation $OP_{SH2}$. Hence, even if the second sampling driving operation $OP_{SH2}$ is suspended in the middle of its operation, the sampling of the sensor signal will be performed appropriately as long as the operation is subsequently restarted and completed. In this point of view, since the sampling of each sensor signal that needs to be actually read out will be performed by the second sampling driving operation $OP_{SH2}$ executed from time t130 to time t140, the second sampling driving operation $OP_{SH2}$ executed from time t107 to time 108 can be referred to as a dummy sampling operation, in this ease, the second sampling driving operation $OP_{SH2}$ executed from time t107 to time 108 may also be referred to as a preliminary driving operation, a preparatory driving operation, a dummy driving operation, or the like.

Figure 6B:
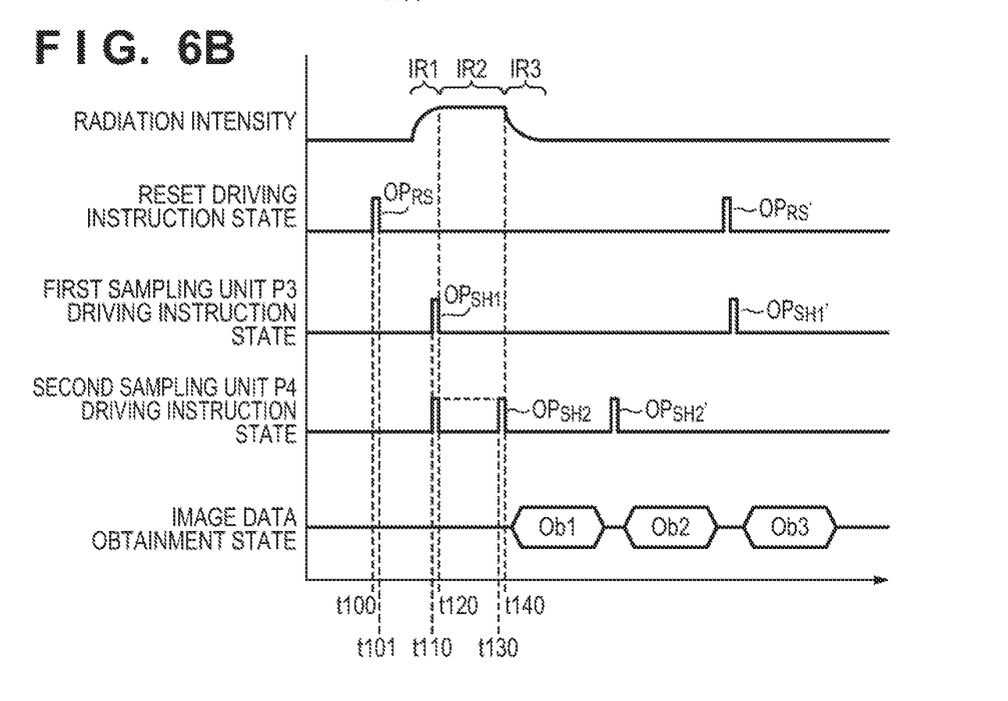
FIG. 6B is a timing chart showing an example of the driving method of the radiation imaging apparatus.

FIG. 6B is a timing chart shoving another example of the driving method of the sensor unit S according to the second embodiment. In this example, both the first sampling driving operation $OP_{SH1}$ and the second sampling driving operation $OP_{SH2}$ are started at time t110 after the completion of the reset driving operation $OP_{RS}$. Subsequently, at time t120, the first sampling driving operation $OP_{SH1}$ is completed and the second sampling driving operation $OP_{SH2}$ is suspended. Thereafter, the second sampling driving operation $OP_{SH2}$ is restarted at time t130, and the second sampling driving operation $OP_{SH2}$ is completed at time t140.

That is, the driving unit 12 sets the control signal SH2 to the inactive level over predetermined period from the timing (time t120) at which the control signal SH1 is set to live inactive level. In this example, the second sampling driving operation $OP_{SH2}$ is suspended by maintaining the control signal SH2 at the inactive level during the period of time t120 to time t130, and the suspended second sampling driving operation $OP_{SH2}$ is restarted from time t130 and onward. This kind of driving method can also allow the first sampling driving operation $OP_{SH1}$ to be performed under an appropriate sampling characteristic. Note that since the sampling of each sensor signal that needs to be actually read out will be performed by the second sampling driving operation $OP_{SH2}$ executed from time t130 to time t140 in this example as well, it can be said that the second sampling driving operation $OP_{SH2}$ executed from time t110 to time 120 is performed as a dummy sampling operation.

Although the sampling units P3 and P4 have also been discriminated and described as separate elements in this embodiment as well, in a similar manner to the first embodiment, these sampling units need not be arranged individually so as to allow discrimination and may be formed by a single element. That is, in this embodiment as well, a single sampling unit that can execute, at least, a plurality of sampling driving operations in parallel and can independently execute the first sampling driving operation $OP_{SH1}$ and the second sampling driving operation $OP_{SH2}$ can be arranged in each sensor unit S. In this embodiment as well, the driving unit 12 can use, in a similar manner to the first embodiment, such a sampling unit to perform the first sampling driving operation $OP_{SH1}$ and the second sampling driving operation $OP_{SH2}$ to sample each signal propagating through the signal line L02. Also, in this embodiment, the driving unit 12 can suspend the second sampling driving operation $OP_{SH2}$ over a predetermined period (from time t108 to time t130 in the example of FIG. 6A and from time t120 to time t130 in the example of FIG. 6B). Alternatively, the driving unit 12 can drive this sampling unit before the completion of the first sampling driving operation $OP_{SH1}$ to perform a preliminary driving operation (or a preparatory driving operation or a dummy driving operation) different from the second sampling driving operation $OP_{SH2}$ performed from time t130 to time t140. This preliminary driving operation corresponds to the second sampling driving operation $OP_{SH2}$ performed from time t107 to time t108 in the example of FIG. 6A and that performed from time t110 to time t120 in the example of FIG. 6B.

Other Embodiments

Although several preferred embodiments have been exemplified above, the present invention is not limited to these examples and can also be changed without departing from the spirit and scope of the invention. For example, the contents of the embodiments can be combined with each other, and well-known elements can be alternatively/incidentally added or deleted as needed.

For example, a sensor array 11 may be made by using amorphous silicon or the like, a PIN sensor, a MIS sensor or the like may be used as a detection element PD of each sensor unit S, and a thin-film transistor or the like may be used as a transistor M11 or the like. Also, although an indirect conversion method sensor array 11 was exemplified in above-described embodiments, a method in which radiation is directly converted into electrical signals, that is, the so-called direct conversion method may be applied to the sensor array 11.

According to the present invention, a signal sampling accuracy of each sensor unit in a sensor array can be improved.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
    a sensor array in which a plurality of sensors are arranged so as to form a plurality of rows and a plurality of columns; and
    a driver configured to drive the sensor array;
    each of the plurality of sensors including a detector configured to detect radiation, a first sampler configured to sample a signal from the detector, and a second sampler configured to sample a signal from the detector;
    each of the first and second samplers being connected to a signal line configured to propagate a signal from the detector, the driver being configured to use the first and second samplers to respectively perform first and second sampling driving operations to sample the signal propagating through the signal line, the driving operations employing an energy subtraction method using first image data based on signals sampled in the first sampling driving operation and second image data based on signals sampled in the second sampling driving operation, and the driver being configured to start the second sampling driving operation before the completion of the first sampling driving operation and being configured to complete the second sampling driving operation after the completion of the first sampling driving operation.

2. The radiation imaging apparatus according to claim 1, wherein the driver is configured to perform a reset driving operation to reset the first sampling unit and the second sampling unit before the start of radiation irradiation on the sensor array, the driver is configured to perform the first sampling driving operation, after the completion of the reset driving operation and after the start of the radiation irradiation, using the first sampler to sample the signal propagating through the signal line, and the driving unit is configured to perform the second sampling driving operation using the second sampler to sample the signal propagating through the signal line.

3. The radiation imaging apparatus according to claim 2, wherein a signal for driving the first sampler is set as a first driving signal and a signal for driving the second sampler is set as a second driving signal, and the driver is configured to start the first sampling driving operation by setting the first driving signal at an active level and is configured to complete the first sampling driving operation by setting the first driving signal at an inactive level, and the driver is configured to start the second sampling driving operation by setting the second driving signal at the active level and is configured to complete the second sampling driving operation by setting the second driving signal at the inactive level.

4. The radiation imaging apparatus according to claim 3, wherein the driver is configured to perform the first and second sampling driving operations such that a period in which the first driving signal is maintained at the active level and a period in which the second driving signal is maintained at the active level will overlap each other.

5. The radiation imaging apparatus according to claim 4, wherein the driver is configured to perform the first and second sampling driving operations such that a timing at which the second driving signal is set to the active level will be a timing after the first driving signal is set to the active level and before a timing at which the first driving signal is set to the inactive level.

6. The radiation imaging apparatus according to claim 4, wherein the driver is configured to perform the first and second sampling driving operations such that a timing at which the first driving signal is set to the active level and a timing at which the second driving signal is set to the active level will match each other.

7. The radiation imaging apparatus according to claim 4, wherein the driver is configured to perform the first and second sampling driving operations by setting the second driving signal to the active level before a timing at which the first driving signal is set to the active level, and setting the second driving signal to the inactive level after a timing at which the first driving signal is set to the inactive level.

8. The radiation imaging apparatus according to claim 6, wherein the driver is configured to suspend the second sampling driving operation by setting the second driving signal to the inactive level over a predetermined period from a timing at which the first driving signal is set to the inactive level.

9. The radiation imaging apparatus according to claim 7, wherein the driver is configured to suspend the second sampling driving operation by setting the second driving signal to the inactive level over a predetermined period from before the timing at which the first driving signal is set to the active level until after the timing at which the first driving signal is set to the inactive level.

10. The radiation imaging apparatus according to claim 1, wherein each of the plurality of sensors includes a signal amplification unit configured to amplify the signal of the detection element and output the amplified signal to the signal line.

11. A radiation imaging system, comprising:
the radiation imaging apparatus according to claim 1; and
a radiation source configured to generate radiation.

12. The radiation imaging apparatus according to claim 1, wherein the first and second samplers are respectively configured to perform the first and second sampling driving operations during a single radiation irradiation operation performed in a predetermined period.

13. The radiation imaging apparatus according to claim 1, wherein the signal sampled in the first sampling driving operation is a signal that corresponds to a first period in which a radiation intensity changes to increase with time, the signal sampled in the second sampling driving operation is a signal that corresponds to a second period including the first period, and a period after the first period and before a period in which a radiation intensity changes to decrease with time, and the signal sampled in the first sampling driving operation and the signal sampled in the second sampling driving operation are read out by a non-destructive readout method.

14. The radiation imaging apparatus according to claim 1, wherein during radiation irradiation for one time, the driver starts the second sampling driving operation before the completion of the first sampling driving operation, and completes the second sampling driving operation after the completion of the first sampling driving operation.

15. A radiation imaging apparatus, comprising:
a sensor array in which a plurality of sensors are arranged so as to form a plurality of rows and a plurality of columns; and
a driver configured to drive the sensor array;
each of the plurality of sensors including a detector configured to detect radiation, a first sampler configured to sample a signal from the detector, and a second sampler configured to sample a signal from the detector, wherein
each of the first and second samplers are connected to a signal line configured to propagate a signal from the detector,
the driver is configured to use the first and second samplers to respectively perform first and second sampling driving operations to sample the signal propagating through the signal line, the driving operations employing an energy subtraction method using first image data based on signals sampled in the first sampling driving operation and second image data based on signals sampled in the second sampling driving operation, and the driver is configured to drive the second sampler to start a preliminary sampling driving operation that is different from the second sampling driving operation, before the completion of the first sampling driving operation.

16. The radiation imaging apparatus according to claim 15, wherein the driving unit performs a reset driving operation to reset the first and second samplers before the start of radiation irradiation on the sensor array,
the driver is configured to perform the first sampling driving operation, after the completion of the reset driving operation and after the start of the radiation irradiation, using the first sampler to sample the signal propagating through the signal line,
the driver is configured to perform the second sampling driving operation using the second sampler to sample the signal propagating through the signal line, and
the driver is configured to drive the second sampler to perform the preliminary driving operation before the completion of the first sampling driving operation.

17. A radiation imaging system, comprising:
the radiation imaging apparatus according to claim 15; and
a radiation source configured to generate radiation.

18. The radiation imaging apparatus according to claim 15, wherein the first and second samplers are respectively configured to perform the first and second sampling driving operations during a single radiation irradiation operation performed in a predetermined period.

19. An arithmetic processing apparatus, comprising at least one processor circuit with a memory comprising instructions, that when executed by the processor circuit, cause the at least one processor circuit to perform an arithmetic processing based on an energy subtraction method using a plurality of sets of image data based on signals sampled in sampling driving operation;
the plurality of sets of image data being obtained based on first and second sampling driving operations;
the first sampling driving operation sampling a signal corresponding to a first radiation dose; and
the second sampling driving operation sampling a signal corresponding to a second radiation dose different from the first radiation dose, wherein
the second sampling driving operation is started before the completion of the first sampling driving operation.

20. A method for performing an arithmetic processing based on an energy subtraction method using a plurality of sets of image data based on signals sampled in sampling driving operation, comprising the steps of:
obtaining the plurality of sets of image data based on first and second sampling driving operations;
the first sampling driving operation sampling a signal corresponding to a first radiation dose; and
the second sampling driving operation sampling a signal corresponding to a second radiation dose different from the first radiation dose, wherein
the second sampling driving operation is started before the completion of the first sampling driving operation.

21. A non-transitory computer-readable storage medium storing a program for causing a computer to execute the method according to claim 20.

* * * * *